United States Patent [19]

Fox, Jr., deceased et al.

[11] Patent Number: 5,334,588
[45] Date of Patent: Aug. 2, 1994

[54] COMPOSITION FOR INHIBITING TRANSMISSION OF HEPATITIS B VIRUS

[75] Inventors: Charles L. Fox, Jr., deceased, late of Fort Lauderdale, Fla., by Alan F. Ruf, legal representative; Shanta M. Modak, River Edge, N.J.

[73] Assignee: The Trustees of Columbia University in the City of New York, Morningside Heights, N.Y.

[21] Appl. No.: 678,260

[22] PCT Filed: Oct. 17, 1989

[86] PCT No.: PCT/US89/04642

§ 371 Date: Jun. 4, 1991

§ 102(e) Date: Jun. 4, 1991

[87] PCT Pub. No.: WO90/04390

PCT Pub. Date: May 3, 1990

Related U.S. Application Data

[63] Continuation-in-part of Ser. No. 262,165, Oct. 18, 1988, Pat. No. 4,952,411, which is a continuation-in-part of Ser. No. 18,624, Feb. 25, 1987, abandoned.

[51] Int. Cl.$^5$ .................... A61K 31/56; A61K 31/555
[52] U.S. Cl. .................... 514/171; 514/184
[58] Field of Search ............. 514/169, 495, 635, 171, 514/184; 424/618

[56] References Cited

U.S. PATENT DOCUMENTS

| | | | |
|---|---|---|---|
| 3,761,590 | 9/1973 | Fox, Jr. | 514/157 |
| 4,415,565 | 11/1983 | Wysor | 514/184 |
| 4,581,028 | 4/1986 | Fox, Jr. et al. | 514/157 |
| 4,612,337 | 9/1986 | Fox, Jr. et al. | 514/157 |
| 4,666,896 | 5/1987 | Warner, Jr. et al. | 514/635 |
| 4,952,411 | 8/1990 | Fox, Jr. et al. | 514/635 |

OTHER PUBLICATIONS

Volk, Wesley A. "Essentials of Medical Microbiology" 2nd edition (1982) p. 130.
Martindale, The Extra Pharmacopoeia, 28th edition (1982) pp. 554-556.
Chem. Abstracts 83: 716206; (1975).
Wysor, Antibiotics, vol. VI, Springer-Verlag Berlin pp. 200-232 (1983).
Chem. Abstracts 102(15);12821; (1985) Boudouma et al.
Chem. Abstracts 101(19) 221999p (1984) Queno et al.

*Primary Examiner*—Raymond J. Henley, III
*Attorney, Agent, or Firm*—Brumbaugh Graves Donohue & Raymond

[57] ABSTRACT

The present invention relates to methods of inhibiting transmission of Hepatitis B virus using compositions comprising silver sulfadiazine and preferably further comprising a biguanide such as chlorhexidine and/or a detergent such as sodium deoxycholate. It is based, at least in part, on the discovery that silver sulfadiazine alone or in combination with chlorhexidine or sodium deoxycholate was shown to inhibit Hepatitis B virus DNA synthesis. The inhibitory effect of silver sulfadiazine was enhanced by combining silver sulfadiazine with either chlorhexidine or sodium deoxycholate.

9 Claims, 1 Drawing Sheet

COMPOSITION FOR INHIBITING TRANSMISSION OF HEPATITIS B VIRUS

DESCRIPTION

This application is a continuation-in-part of U.S. Patent application Ser. No. 07/262,165 filed Oct. 18, 1988 now U.S. Pat. No. 4,952,411 which is a continuation-in-part of U.S. Patent application Ser. No. 07/018,624 filed Feb. 25, 1987 now abandoned.

BACKGROUND OF THE INVENTION

The present invention relates to compositions for inhibiting the transmission of Acquired Immunodeficiency Syndrome (AIDS).

AIDS is a fatal catastrophic disease that presently infects millions of people worldwide. Although initially concentrated in central Africa and in certain high risk groups in other geographic areas including the United States, AIDS is now spreading to other areas and is appearing in individuals who are not members of the recognized risk groups. As a result, major efforts are being made to develop methods of preventing the transmission of AIDS, methods of curing AIDS once contracted, and methods of ameliorating the symptoms of AIDS. To date, however, AIDS has proven difficult to treat or prevent.

AIDS is caused by a virus. This virus has been referred to by a number of names in the literature, including HIV (human immunodeficiency virus), LAV (lymphadenopathy-associated virus), ARV (AIDS-related virus) and HTLV-III (human T-cell leukemia virus-III). For simplicity, the virus causing AIDS will be referred to herein as the AIDS virus.

It is generally known that viruses can be divided into two groups based upon the nature of the virus' genetic material. Some viruses are DNA viruses, that is, their genetic material is deoxyribonucleic acid, while others are RNA (ribonucleic acid) viruses. The RNA viruses can further be divided into two groups, those in which replication of the vital genome proceeds by making an RNA copy directly from the RNA genome and those in which a DNA intermediate is involved. This latter type of RNA virus is called a retrovirus.

The AIDS virus is a retrovirus. Thus, like other retroviruses, it has an enzyme called reverse transcriptase (or RNA-dependent DNA polymerase) which catalyzes transcription of viral RNA into double helical DNA. This DNA sequence is integrated into the genome of the infected cell where it is known as a provirus. Subsequent transcription of this provirus by the transcription mechanism of the infected cell produces new vital RNA for packaging into new virus particles.

Because the AIDS virus may lie dormant in an infected cell in the form of a provirus for extended periods of time, it has been difficult to establish the precise routes by which AIDS is spread. It is known, however, that AIDS can be transmitted to a person by transfusing that person with blood containing the AIDS virus. AIDS can also be transmitted to a person through homosexual or heterosexual intercourse with a partner infected with the AIDS virus. Transmission of the AIDS virus is facilitated by preexisting sexually transmitted diseases (STD's) other than AIDS, for example gonorrhea. Further, scientists suspect that the AIDS virus is spread easily during sexual intercourse due to tearing of tissue which would abet entry of the AIDS virus into the blood stream.

In response to the growing threat of AIDS transmission, the use of condoms during sexual intercourse has been suggested as a means of preventing transmission of the AIDS virus. Improper use of condoms, or their perforation during intercourse renders them only partially effective. Accordingly, there is a pressing need for a better method of inhibiting the transmission of the AIDS virus in humans during sexual intercourse and during surgical procedures on infected patients. It is an object of the present invention to provide such a method.

SUMMARY OF THE INVENTION

The present invention provides an inexpensive, easily available and convenient composition for inhibiting the transmission of the AIDS virus in humans for example, as a result of sexual intercourse. The invention relies upon a dual mode of action of particular compounds and combinations thereof which results in a rapid killing action within minutes. These compounds are effective to reduce the infectivity of the AIDS virus and also to kill the causative organisms of many other STD's after short exposure. The method of the invention is therefore useful to reduce the immediate risk of AIDS transmission. It also reduces future risk of AIDS transmission by eliminating STD causing organisms which increase the risk of AIDS. The present invention also provides for methods of inhibiting transmission of Hepatitis B virus (HBV).

Silver salts, such as silver sulfadiazine (AgSD), are among the compounds found to be effective antiviral agents against retroviruses including the AIDS virus. Such materials had previously been recognized as antibacterial agents useful in treating burns in man and animal. C. L. Fox, Jr., U.S. Pat. No. 3,761,590. AgSD has also been shown to be effective against certain viruses such as herpes simplex and herpes zoster and against the causative organisms of many STD's including *Candida albicans, Treponema pallidum* and gonorrhea. U.S. Pat. No. 4,415,565 of Wysor shows further antiviral activity of AgSD against certain RNA viruses, but none of these are retroviruses. Thus, while AgSD is a well studied material, there was no basis to expect that it would have activity against the AIDS retrovirus which has proven so difficult to inhibit or destroy.

Biguanides, such as chlorhexidine, have also been found to be effective when used at sufficiently high levels as inhibitors of the AIDS virus.

We have also found that combinations of these compounds with each other and with other antibacterial agents lead to an unexpected enhancement of the antiviral activity of AgSD and also in a rapid killing action. Specifically, AgSD in combination with chlorhexidine, a broad spectrum antibacterial agent, is substantially more effective for reducing the infectivity of the AIDS virus than AgSD alone, despite the fact the chlorhexidine alone has no effect on infectivity of AIDS virus under the same conditions. Increased effectiveness was also noted for combinations of AgSD with detergents such as deoxycholate.

In view of these findings, the invention contemplates inhibiting the transmission of AIDS comprising topically applying an effective antiviral amount of biguanide or a silver salt such as silver sulfadiazine, alone or in combination. Other agents such as deoxycholate may also be used. The composition is advantageously administered to a sexual canal of a human prior to or during sexual intercourse. This application can be carried out by introducing a cream or foam into the sexual canal, or by coating the inhibitory composition onto a condom or other device that is inserted into the sexual canal.

DETAILED DESCRIPTION OF THE INVENTION

Figure 1:
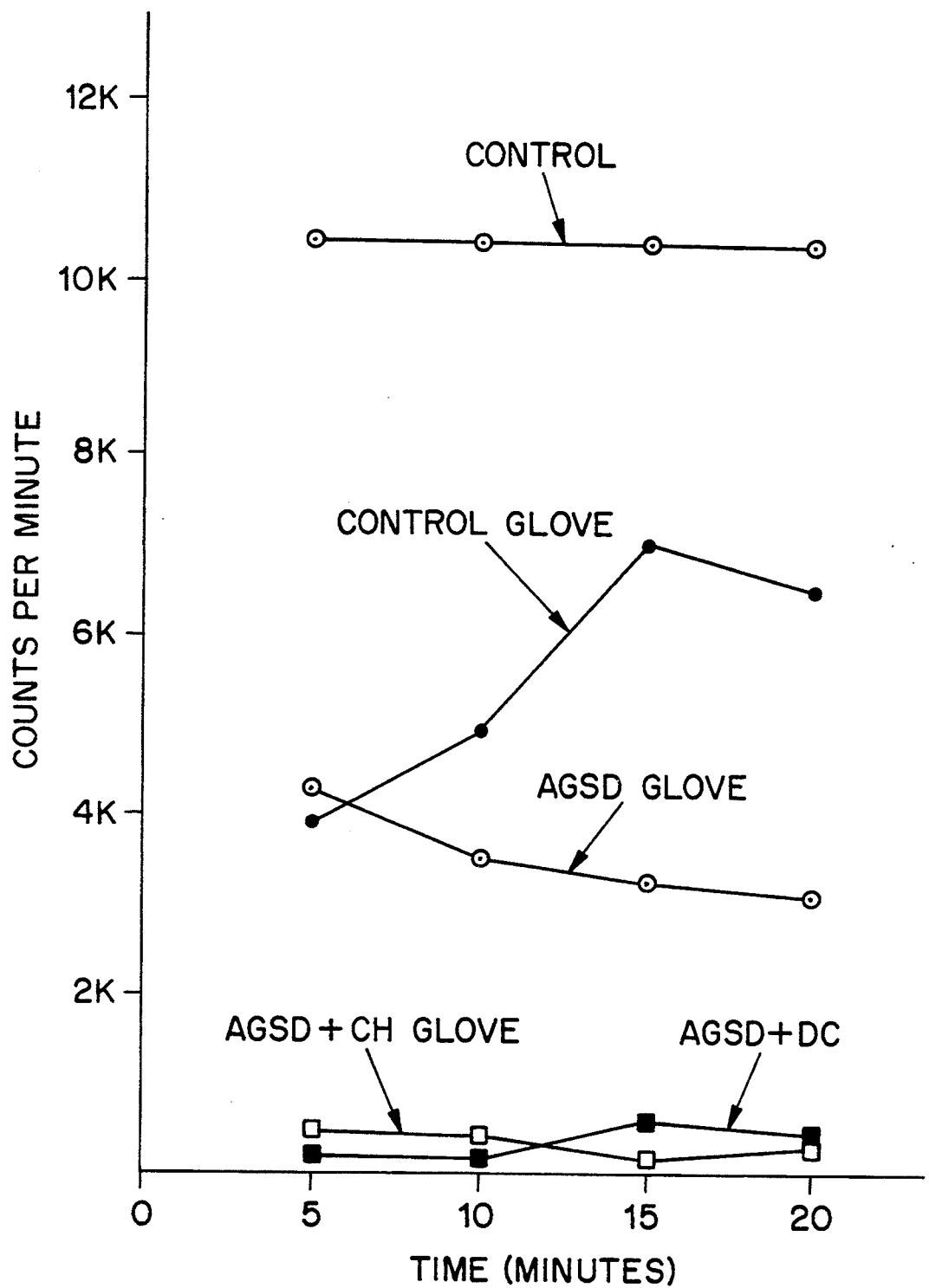
FIG. 1 is a graph of the rate of incorporation of radiolabeled thymidine by hepatitis B virus following exposure of the virus to AgSD alone or in combination with other agents.

As noted above, the composition of the present invention is effective to inhibit the transmission of AIDS virus in humans and other mammals when applied topically in an effective antiviral amount. The composition comprises a biguanide, alone or in combination with other active ingredients.

As used in this application, the term sexual canal refers to either a vaginal or an anal canal.

The antiviral composition used in the method of the invention comprises biguanide, such as chlorhexidine or a salt thereof.

The composition may also include a silver salt. While the examples hereinbelow use one specific silver salt, AgSD, other silver salts may also be used. Other suitable silver salts include silver acetate, silver benzoate, silver carbonate, silver chloride, silver iodate, silver iodide, silver lactate, silver laurate, silver nitrate, silver oxide, silver palmirate, and silver salts of proteins.

The antiviral composition of the invention preferably also comprises one or more additional ingredients which enhance the antiviral effectiveness of the silver salt. Thus, the antiviral composition may contain detergents such as deoxycholate or benzalkonium chloride. Suitable salts of these materials may also be used.

The antiviral composition may also include other materials which are effective against STD-causing organisms which will reduce the long term risk of AIDS infection. Examples of such materials include nonoxynol, which is effective against gonococcus and quinolones which are effective against numerous STD-causing organisms. It should be noted that chlorhexidine and the detergents noted above are also effective against a variety of STD-causing organisms, including herpes simplex virus (HSV), Hepatitis B virus (HBV) and *Candida albicans*. As demonstrated infra in Example 6, AgSD alone or in combination with chlorhexidine or sodium deoxycholate was shown to inhibit HBV DNA synthesis. As shown in FIG. 1, the inhibitory effect of AgED was enhanced by combining AgED with either chlorhexidine or sodium deoxycholate. Accordingly, the present invention provides for methods of inhibiting transmission of HBV using compositions comprising AgSD and preferably further comprising a biguanide such as, for example, chlorhexidine and/or a detergent such as, for example, sodium deoxycholate.

The antiviral compositions for use in the invention can be applied as (a) a dispersion in a water-dispersible hydrophilic carrier; (b) as a dispersion in a substantially water insoluble carrier; (c) as a dispersion in a semi-soft or cream-like water-dispersible or water-soluble oil-in-water emulsion carrier; or (d) as a dispersion in an aqueous sucrose carrier, e.g. an approximately 25%–50% by weight aqueous sucrose solution. Specific examples of formulating silver sulfadiazine in various carriers are provided in U.S. Pat. No. 3,761,590 which is incorporated herein by reference. The carrier will preferably contain from about 0.1 to about 10% by weight of the silver salt and up to 2% of other active agents.

The antiviral composition useful in the method of the invention can be contained in a squeezable tube having an applicator nozzle. This facilitates topical application of the composition to the sexual canal prior to intercourse by inserting the nozzle into the sexual canal and squeezing the tube to force the antiviral composition into the sexual canal. Alternatively, the antiviral can be applied with any of various known applicators for delivering drugs into a sexual canal. The antiviral composition can also be topically applied during sexual intercourse by coating the penis itself or coating a condom with a lubricant material, such as K-Y Jelly (Johnson & Johnson), that contains the silver salt.

The antiviral composition of the invention may also be introduced into the sexual canal as a coating on a device intended for insertion in the sexual canal. Examples of such devices include condoms, medical gloves, and diaphragms. Such devices may be coated or impregnated with the antiviral composition by spraying the completed device or by incorporating the antiviral composition during manufacture. Specific techniques for preparing the devices are described in U.S. patent application Ser. No. 154,920, filed Feb. 11, 1988, and its continuation-in-part filed Oct. 14, 1988, both of which are incorporated herein by reference.

Coating compositions can be made based upon polymeric carriers containing polyurethane or silicons. For example, a coating composition for use on condoms in accordance with the invention can be prepared by combining chlorhexidine acetate (CHA) and N-ethyl-2-pyrrolidone (NEP) and heating to dissolve the CHA. Tetrahydrofuran (THF) is then mixed to the CHA solution in NEP and the mixture is thoroughly added to form a uniform solution. A polyurethane such as Pellethane ® 2363-80AE (Dow Chemical Co.) is dissolved with heat in THF and a silver sulfadiazine powder may then be added to form a suspension. The CHA/NEP solution and the polyurethane suspension are then combined to form the coating composition.

Silicones can be used to provide a coating which is lubricious and releases the drug in a controlled dosing manner. Mixtures of Silastic ® Medical Adhesive Type A, a polydimethyl siloxane, and MDX-4-4159, a fluid silicone comprising equal parts of an amino functional polydimethyl siloxane copolymer and a mixed aliphatic and isopropanol solvent are suited as polymeric coating agents. A 1:1 mixture of these silicones provides a film with desirable biocompatible characteristics.

The experimental results which demonstrate the effectiveness of the claimed method are set forth below. These tests involve the AIDS virus, a recognized model system for the AIDS virus or a recognized STD organism. Further, although the tests with the AIDS virus itself are necessarily in vitro tests in view of the catastrophic consequences of AIDS, these in vitro tests are highly predictive of and correlate with in vivo efficacy. They thus support the surprising finding that compositions containing biguanides with or without silver salts can be used to inhibit transmission of AIDS as a result of sexual intercourse.

EXAMPLE 1

The effectiveness of AgSD against the AIDS virus J1 in vitro was assessed by testing the infectivity of samples of HTLV-III in H9 cells after exposure to AgSD for 10 minutes. Due to the relatively low titers achievable with the AIDS virus, it was necessary to devise means for separating the bulk of the AgSD from the virus to be assayed. After a number of preliminary experiments, it was found that the best method of those investigated was to rapidly pass the AgSD/AIDS virus mixture over a Sephadex G-25M column, recover the AIDS virus containing void volume and precipitate the virus using polyethylene glycol (PEG).

To determine recovery of the virus using this method, a control preparation containing virus but no AgSD was similarly processed.

It was also necessary to confirm that this procedure was effective to remove all of the AgSD. This was accomplished using "Stop Controls". This involved processing AgSD alone through the column, precipitating the same fraction with PEG and then adding active AIDS virus to the precipitate. If the titer of the stop control had been similar to the control preparation containing virus but no AgSD it would have indicated that little or no AgSD was present in the precipitate. In fact, however, the titer was substantially lower in the stop controls (Samples 4 and 6) than in the corresponding test samples without silver sulfadiazine (Samples 1 and 2). This indicates that some of the silver sulfadiazine is not being separated. While this means that virus killing occurred over a longer period than the ten minute contact time, it also suggests that the virucidal activity is fairly strong to persist even at the reduced levels.

The specific tests conducted are summarized in Table 1. For each sample to which virus was added initially, the virus sample was a stock solution prepared from a 10,000 fold concentrate of HTLV-III obtained from Bionetics Research. This material was diluted 1:10 with Conditioned Infection Medium (CIM) to form a stock solution with an actual virus titer of $10^{5.5}$/ml. Two AgSD stock preparations were also prepared, a 1% by weight in 50% by weight aqueous sucrose preparation and an 0.5% by weight in 25% by weight aqueous sucrose preparation.

To conduct the tests, 60 μl aliquots of the virus stock were placed in microfuge tubes as samples 1–3 and 6 as indicated in Table 1. This was mixed with 540 μl of the respective AgSD preparations in tubes 3 and 5 and with 540 μl of CIM in tubes 1 and 2. Tubes 4 and 6 each received 600 μl of the respective AgSD preparations, but no virus. Each tube was then mixed with a vortex mixer and allowed to incubate for 10 minutes at room temperature.

To separate the AgSD from the virus, the contents of each tube containing AgSD then centrifuged in a microfuge for 1 minute, and the supernatants were collected. These supernatants and the entire sample of tube 2 were then introduced onto a Sephadex-25M column. The columns used had a fitted disc at the top of the column and a void volume of approximately 1 ml. These columns are normally stored in sodium azide and had been prepared by washing under sterile conditions with 18 successive 4 ml portions of CIM medium on the day prior to the experiment.

Each of the samples was placed on the column until it passed through the fitted disc. The column was then eluted with 4 ml of CIM medium. The first 3 ml of eluent was discarded and the last ml was collected into a sterile microfuge tube containing 0.35 ml of 30% PEG 6000 in phosphate buffer. These tubes were held at 0° C. for at least 30 minutes and then centrifuged for 1 minute in a microfuge. The pellets were collected and resuspended in either 0.5 ml CIM (samples 2, 3 and 5) or in an HTLV-III containing medium made by diluting 0.7 parts of the virus stock with 6.3 parts of CIM.

Each of the six samples thus prepared was assayed in quadruplicate with 10-fold dilutions in CIM for its ability to infect H9 cells. This was done by adding 50 μl of a preparation containing $2.4 \times 10^6$/ml H9 cells that had been conditioned in CIM for 1 hour at 37° C. to each 100 μl of sample or dilution. This culture was fed 25 μl of CIM on days 4, 7 and 10. On day 4, cytotoxicity was evaluated by visual examination of the cultures.

The results of these observations are shown in Table 1. As can be clearly seen, AgSD substantially reduced the infectivity of AIDS virus tested without any observation of cytotoxicity.

EXAMPLE 2

The effect of AgSD, chlorhexidine and sodium deoxycholate, both individually and in combination, on the infectivity of the ARV-2 strain of AIDS virus was tested in H9 cells using lower concentrations of drug such as can be practically coated onto a glove or condom or other device. These concentrations were below the level that produced substantial observable cytotoxicity, even during incubation with the virus, and yet were effective at killing the virus.

A stock solution of virus containing 3 to $5 \times 10^4$ infectious virus particles/ml was preincubated with the various drugs as indicated in Table 2 for 15 minutes. The virus sample was then diluted 4-fold in order to reduce the concentrations of the drugs below levels toxic to H9 cells (see Example 3 below) and mixed with 250,000 H9 cells in a total volume of 1 ml. After 24 hours, the cells were assayed to determine the percentage of the culture expressing viral antigen. This time interval was selected as it allows for only a single round of viral infection to have occurred such that the number of cells infected was a direct reflection of the number of infectious virions present in the original sample.

As can be seen from Table 2, AgSD alone at these low concentrations was only slightly effective, but better results were obtained when AgSD was used in combination with either sodium deoxycholate and chlorhexidine. Of particular significance is the marked reduction in infectivity observed for the combination of AgSD (5 μg/ml) and chlorhexidine (5 μg/ml) since chlorhexidine (10 μg/ml) did not itself reduce viral infectivity.

EXAMPLE 3

The toxicity of the various agents used in the antiviral compositions of the invention to human $T_4$-lymphocytes (H9 cells and marophocytes which are the carriers of the AIDS virus) may be relevant to the effectiveness of a drug. This is because killing these cells when present in semen or vaginal fluids may lead to release of virus making it more susceptible to the effects of the drug. With this in mind, the effect of short exposure (10 minutes) of AgSD and other drugs on H9 cells was tested by treating a suspension of H9 cells ($1.6 \times 10^6$/ml in HBSS) with 50 and 100 ml/ml of each drug or drug combination. After incubating for 10 minutes, the cells were washed twice in thirty volumes of HBSS; resuspended in RPMI 10% FCS+NaPyruvate and plated into 24 well plates at $4 \times 10^5$ cells/mi. Cell viability was determined after 24 hours and is reported as numbers of viable cells per ml and viable percentage (live cells/live cells+dead cells) in Table 3A. As can be seen, each of the agents tested kills some of the cells, although the most significant killing is observed for 100 µl/ml AgSD and the combination of AgSD and sodium deoxycholate.

The effectiveness of killing of macrophages was also tested as shown in Table 3B. In the experiment, peritonial normal mouse macrophages were enriched by attaching to petri dishes and adjusted to a cell concentration of 5 to $10 \times 10^6$/ml. 0.1 ml aliquots of this suspension were plated in microtiter plates and 10µ and 5µ of each of four samples was added. The control plate received PBS only. After 20 minutes of incubation in a CO incubator, the cells were tested for viability using tryphan-blue dye. The percent kill is shown in Table 3B.

EXAMPLE 4

In vivo tests were performed using Rauscher Leukemia Virus (RLV), a recognized retrovirus model (see, e.g., Nature 323, 467–469 (1986); Rupecht et al., Proc. Nat'l. Acad. Sci. USA 82, 7733–7737 (1985)) which is used by the FDA in testing drugs for use in treating AIDS. RLV was introduced into Balb/CICR mice in which it infects the spleen. The level of virus infectivity was quantified by determining the weight increase of the mouse spleen after 20 days from infection.

A preliminary experiment was first carried out to determine the effect of the drugs to be tested on the spleen. Nine sets of five mice each (6 week old female mice) received 0.25 ml injections into the tail vein of one of an extract of a glove treated with one of the following solutions:

1. Silver Sulfadiazine (2%)
2. Sodium Deoxycholate (2%)
3. Chlorhexidine (2%)
4. Silver Sulfadiazine (1%)+Sodium Deoxycholate (1%)
5. Silver Sulfadiazine (1%)+Chlorhexidine (1%)
6. Fusidic Acid (2%)
7. Fusidic Acid (1%)+Chlorhexidine (1%)
8. Saline incubated glove
9. Saline-no glove Each treatment was prepared by incubating 1.5 ml Dulbecco's Phosphate Buffered Saline (PBS) for 10 minutes at 37° C. in the finger tip of a latex glove. After incubation, as much as possible of the material was removed from the glove. 0.4 ml of PBS was then introduced into the glove and this was the sample which was introduced into the animals. The animals that did not receive a clean stick during the injection were excluded from the study. Thus two of the groups only had four animals each that were considered.

Eight days after injection each of the animals was sacrificed and the spleen weights determined for each animal. No increase in spleen weight was observed in any of the groups.

An additional eleven groups of 5 mice each were then used to test the effectiveness of these same compounds against infectivity of RLV. Each treatment was prepared by incubating 0.4 ml sterile PBS containing RVB3 (a strain of RLV) for 10 minutes in a glove tip which had previously had one of drugs or straight PBS incubated in it as described above. Three additional controls, a PBS containing glove with no virus, a virus sample not incubated in a glove, and a PBS sample not incubated in a glove were also run. The mice in this case were sacrificed 20 days after injection and spleen weights determined as shown in Table 4. Each of the materials tested showed a substantial reduction in virus infectivity.

EXAMPLE 5

The combination of AgSD with chlorhexidine and deoxycholate was also found to be particularly effective against several STD-causing organisms. As shown in Tables 5A and 5B silver sulfadiazine in combination with chlorhexidine or sodium deoxycholate is particularly effective against Candida albicans. Similarly, these combinations are effective to kill Gonococcus (Table 6) and herpes virus (Tables 7A and 7B).

EXAMPLE 6

The effect of AgSD alone or in combination with chlorhexidine or sodium deoxycholate on DNA synthesis by Hepatitis B Virus was studied by measuring the rate of incorporation of radiolabeled thymidine. As a result, it was found that the AgSD interferes with the RNA-dependent DNA polymerase of Hepatitis B virus, an interference which is enhanced by using it in combination with either chlorhexidine or sodium deoxycholate (FIG. 1).

EXAMPLE 7

The effect of chlorohexidine on HIV-I was tested by researchers at Stuart Pharmaceuticals, Wilmington, Del. using a 4% chlorhexidine gluconate (CHG) hand scrub (HIBICLENS®) and an 0.5% CHG-containing hand rinse (HIBISTAT®). In each case, an HIV-I preparation was exposed to dilutions of one of the two materials for 10 minutes after which the viral preparation was used to infect C3-44 cells. The presence of HIV-I infection was monitored by indirect immunofluorescense by detecting vital p24 antigen expression and by reverse transcriptase activity in culture fluid as a measure of virus production. The results of this experiment showed that, chlorhexidine gluconate at concentrations of 0.04%, 0.05% and higher were effective to prevent HIV-I infection, while concentrations of 0.01% and lower were not. Thus, it appears that a threshold level of chlorhexidine is necessary for activity and that the results in Example 2 can be attributed to the use of chlorhexidine at a level below this threshold.

EXAMPLE 8

A silicone coating agent was prepared by dispersing 2.5 ml of Silistic® Medical Adhesive Type A in 55 ml of THF to which 2.5 ml of MDX-4-4159 is added. 4 g of AgSD are suspended in 30 ml and 2 g of CHA are dissolved in 10 ml of ethanol. The AgSD suspension is mixed with the silicone dispersions and finally the CHA solution is added dropwise while the preparation is agitated. Either 5% NEP or 5% DMAC can be substituted for ethanol in the above formulation.

The coating agent prepared above was used to apply a coating on catheters fabricated from silicone, polyurethane and latex substrates. The coatings were applied by dipping and then drying. Results are given in Table 8 below.

TABLE 8

Antibacterial Efficacy of Polyurethane I.V. Catheters and Latex or Silicone Urinary Catheters Coated with A silicone Matrix

| Catheter Type | Drug in Catheter | Days of Activity* |
|---|---|---|
| Polyurethane I.V. | CHA | 2 |
| Polyurethane I.V. | AgSD + CHA | 4 |

TABLE 8-continued

Antibacterial Efficacy of Polyurethane
I.V. Catheters and Latex or Silicone Urinary
Catheters Coated with A silicone Matrix

| Catheter Type | Drug in Catheter | Days of Activity* |
|---|---|---|
| Latex urinary | AgSD | 2 |
| Latex urinary | AgSD + CHA | 4 |
| Silicone urinary | AgSD | 3 |
| Silicone urinary | AgSD + CHA | 4 |

*Determined via Bioassay A. Inoculum used to assay urinary catheter is a $10^4$ CFU of a 1:1 mixture of Staph. epi and E. coli; $10^4$ CFU of Staph. aureus is used to challenge the I.V. catheter.

EXAMPLE 9

The fingers of latex gloves were washed and dried. They were then sprayed with a fine mist spray of a coating solution to provide a uniform coating of solution on the glove surface, sufficient to provide complete wetting thereof without runoff. The coating solutions were prepared by dissolving 1% Silicate ®Medical Adhesive Type A and 1% of the silicone MDX4-4159 in ethyl acetate, followed by dissolving and dispersing the chlorhexidine acetate and silver sulfadiazine, respectively, therein. The coating was air dried for 24 hours and the gloves tested using the following test:

Treated glove fingers were draped over the tops of culture tubes with the treated side with sprayed on coating forming the inside of the cup shape. Then 3.0 ml of TSB containing $10^4$ colony forming units of Staph. aureus was dispensed in each finger and all placed in a water bath shaker at 37° C. Samples were removed at 15 minutes, 1 hour, 2 hours, and 4 hours, diluted 1–10, and the solution plated on blood agar in 2.0 ml amounts.

The results of the test are summarized in the following Table 9.

TABLE 9

Antibacterial Efficacy of Drug Coated
Gloves against Staph. aureus

| Drug in Coating Solution | Colony Counts in Culture | | | |
|---|---|---|---|---|
| | 15 min. | 1 hour | 2 hours | 4 hours |
| None (Control) | 12,000 | 15,000 | 20,000 | 50,000 |
| Chlorhexidine (1%) | 100 | 0 | 0 | 0 |
| Silver Sulfadiazine (2%) | 3,300 | 200 | 0 | 0 |
| Silver Sulfadiazine (1%) + Chlorhexidine (1%) | 0 | 0 | 0 | 0 |

It is noted that the gloves coated according to this procedure were flexible and met all other requirements for high quality latex gloves.

TABLE 1

ASSAY MIXTURES AND RESULTS

| Sample No. | Material | HTLV-III (Stock 21) 10-1 | Mixture CIM | AgSD | Stop Procedure | PEG Pellet Resuspended in (0.5 ml) | Log$_{10}$** TCID$_{50}$ Per/ml | Log*** Kill | Cytotoxicity |
|---|---|---|---|---|---|---|---|---|---|
| 1 | HTVL-III (Stock 21) ($10^{-1}$) | 60 ul | 540 ul | — | — | — | 4.5 | — | 0 |
| 2 | HTVL-III (Stock 21) ($10^{-1}$) | " | " | — | Column + Peg | CIM | 4.25 | — | 0 |
| 3 | 1% AgSD in 50% aqueous sucrose solution | " | — | 540 | Cent.* + Peg | CIM | 2.0 | 2.25 | 0 |
| 4 | 1% AgSD in 50% aqueous sucrose solution | — | — | 600 | " | $10^{-2}$ HTLV-III (Stop Control) | 3.25 | — | 0 |
| 5 | 0.5% AgSD in 25% aqueous solution | 60 ul | — | 540 | " | CIM | 2.25 | 2.0 | 0 |
| 6 | 0.5% AgSD in 25% aqueous solution | — | — | 600 | " | $10^{-2}$ HTLV-III (Stop Control) | 3.75 | — | 0 |

*Centrifuge 1 minute in microfuge - place supernatant on column
**TCID$_{50}$ = Tissue Culture Infecting Dose$_{50}$
***Compared to Sample No. 2

TABLE 2

| Drug During Incubation | (µg/ml) | Final (Drug) µg/ml | % Infection | % Infection v. Control |
|---|---|---|---|---|
| chlorhexidine (CHA) | 10 | 2.5 | 3.35 | 108 |
| sodium deoxycholate (NaDC) | 40 | 10.0 | 3.35 | 108 |
| AgSD | 10 | 2.5 | 2.95 | 95 |
| AgSD + NaDC | 10 40 | 2.5 + 10.0 | 2.85 | 92 |
| AgSD + CHA | 5 + 5 | 1.25 + 1.25 | 2.45 | 72 |

TABLE 3A

| | Viable Cells/ml | | % Viab** |
|---|---|---|---|
| *AgSD 50 | 4 × $10^5$ | Cells in terrible condition. | 37 |
| 100 | 5 × $10^4$ | " | 0 |
| CHA 50 | 1.5 × $10^6$ | " | 73 |
| 100 | 2.5 × $10^5$ | " | 20 |
| NaDC 50 | 1.2 × $10^6$ | | 73 |
| 100 | 2.0 × $10^6$ | | 44 |
| AgSD 50 + CHA 50 | 1.5 × $10^4$ | | 0 |
| H$_2$O | 3.1 × $10^6$ | | 89 |

TABLE 3A-continued

| | Viable Cells/ml | % Viab** |
|---|---|---|
| Cells Alone | $3.0 \times 10^6$ | 88 |

*AgSD + insoluble. In an attempt to remove drug cells were spun at 200 g for 15 sec. (including acceleration and deceleration time) + Cell pipetted off, then washed two times.
**live cells/live & dead

TABLE 3B

Results
Rate of Killing of Macrophage by Drugs

| | % Kill |
|---|---|
| Control | 36 |
| AgSD (100 μg) | 100 |
| CHA (100 μg) | 100 |
| AgSD + CHA (50 μg + 50 μg) | 85 |

TABLE 4

Results

| Drug in Glove | Concentration of Drug in Coating Solution (%) | Weight of Spleen (mg) (Average of 6 Animals) | Weight Increase from Control (mg) |
|---|---|---|---|
| Silver sulfadiazine | 2 | 106 | 20 |
| Deoxycholate | 2 | 109 | 23 |
| Chlorhexidine | 2 | 234 | 148 |
| Silver sulfadiazine + deoxycholate | 1 + 1 | 115 | 29 |
| Silver suladiazine + chlorhexidine | 1 + 1 | 103 | 17 |
| Fusidic acid | 2 | 107 | 21 |
| Fusidic acid + Chlorhexidine | 1 + 1 | 319 | 23 |
| Control glove + PBS medium | | 86 | 0 |
| No glove - only PBS medium | | 86 | 0 |
| Control glove + RVB3 | | 1,627 | 1,541 |
| No glove + RVB3 | | 1,280 | 1,194 |

TABLE 5A

Rate of Killing of Candid-albicans by silver sulfadiazine an other agents on short exposure

| Drug | Concentration | Colony Counts in Culture (10 Minute Incubation) |
|---|---|---|
| Silver sulfadiazine | 100 | 10,000 |
| Chlorhexidine | 100 | 30 |
| Deoxycholate | 1,000 | 8,000 |
| AgSD + Chlorhexidine | 50 + 50 | 0 |
| AgSD + Deoxycholate | 100 + 100 | 20 |
| Nonoxynol | 0.2% | >50,000 |
| Control | | >50,000 |

3 ml of Saboraud broth containing $10^5$ organism of Candida albicans were incubated with the above drug. Aliquots were removed at 5 and 10 minute and were subcultured.

TABLE 5B

Antibacterial Efficacy of Drug Coated Gloves against Candida albicans

Treated glove fingers were draped over the top of culture tubes with the treated side foring the inside of the cup shape. Then 3.0 ml of TSB containing $10^3$ organisms of Candida albicans was dispensed in each finger and all placed in the water bath shaker at 37° C. Samples were removed at 15 minutes, 1 hour, 2 hours, and 4 hours. They were diluted 1-10 and plated on blood agar in 2.0 ml amounts.

| Drug in Glove | Colony Counts in Culture | | | |
|---|---|---|---|---|
| | 15 Minutes | 1 Hour | 2 Hours | 4 Hours |
| None (Control) | 1,400 | 2,000 | 4,000 | 6,000 |
| Chlorhexidine | 75 | 0 | 0 | 0 |
| Silver Sulfadiazine | 1,650 | 1,500 | 1,500 | 2,200 |
| Silver Sulfadiazine + Chlorhexidine | 0 | 0 | 0 | 0 |
| Silver Suladiazine + Deoxycholate | 1,500 | 400 | 0 | 0 |
| Silver Suladiazine + Chlorhexidine + Nonoxynol | 0 | 0 | 0 | 0 |

TABLE 6

Killing of Gonococcus by Silver Sulfadiazine and Other Agents

| Drugs | μg/ml | Colony Counts in Culture | |
|---|---|---|---|
| | | 5 Minutes | 10 Minutes |
| AgSD | 100 | 4,000 | 2,000 |
| Deoxycholate | 1,000 | 12,000 | 4,000 |
| Chlorhexidine | 100 | 2,000 | 10 |
| Nonoxynol | 0.1% | 40 | 70 |
| AgSD + Chlorhexidine | 50 + 50 | 0 | 0 |
| AgSD + Deoxycholate | 100 + 1,000 | 10 | 0 |

TABLE 6-continued

Killing of Gonococcus by Silver Sulfadiazine and Other Agents

| Drugs | μg/ml | Colony Counts in Culture | |
|---|---|---|---|
| | | 5 Minutes | 10 Minutes |
| None (Control) | | >50,000 | >50,000 |

Drugs were suspended in 5 ml of cultures containing 105 organisms of gonococccus and incubated. Aliquots were removed at 5 and 10 minute intervals and subcultured for colony counts.

TABLE 7A

Toxicity of Drugs for HSV

One ml HSV at $3 \times 10^6$/ml was incubated with 200 μliters of drugs each 500 μg/ml stock solution. After 20 minutes at R.T., the virus was titered on monolayers of vero cells, incubatwd for 2 hours, then overlayed with methyl cellulose. Virus titers were read after 48 hours. No drug toxicity* was seen in rows titer read in.

| μliters added to 1 ml Virus | Titer | % Inhibition |
|---|---|---|
| 200 AgSD | $5.2 \times 10^5$ | 81 |
| 200 Chlorhexidine | $2.7 \times 10^6$ | 0 |
| 100 AgSD + 100 Chlorhexidine | $1.5 \times 10^4$ | 99.5 |
| 200 NaDC | $3.2 \times 10^6$ | 0 |
| 100 NaDC + 100 AgSD | $1.3 \times 10^6$ | 54 |
| 100 NaDC + 100 Chlorhexidine | $8 \times 10^4$ | 93 |
| 200 Benzalkonium chloride | $5.2 \times 10^4$ | 98 |
| 200 H$_2$O | $2.8 \times 10^6$ | 0 |
| 200 Media | $3.3 \times 10^6$ | 0 |

*Drug conc. in firt row was 4–8 μg/ml

TABLE 7B

Effect of HSV-1 of Interaction with Drug Treated Gloves

HSV-1 w diluted to $3 \times 10^6$ PFU/ml in DME 10% FCS. On ml of virus was placed in sterile drug treated gloves, incubated for 10 min. at room temperature then titred on Vero cells.

| Treatment | Titer (PFU/ml) |
|---|---|
| virus (no glove) | $2.9 \times 10^6$ |
| virus + ccntrol tube | $3.0 \times 10^6$ |
| virus + tube w | $4.3 \times 10^6$ |
| virus + tube x | <10 |
| virus + tube y | <10 |

W = Silver sulfadiazine
X = Silver sulfadiazine + Deoxycholate
Y = Silver sulfadiazine + Chlorhexidine It is claimed:

1. A method for inhibiting transmission of hepatitis B virus, comprising applying to a patient a composition comprising an effective antiviral amount of silver sulfadiazine at a site where contact with hepatitis B virus may occur.

2. A method according to claim 1, in which the composition further comprises a biguanide in an amount such that the combination of silver sulfadiazine and biguanide has an antiviral effect.

3. The method according to claim 2, in which the biguanide is chlorhexidine.

4. The method according to claim 1, in which the composition further comprises chlorhexidine in an amount such that the combination of silver sulfadiazine and chlorhexidine has an antiviral effect.

5. The method according to claim 1, in which the composition further comprises a detergent selected from the group consisting of sodium deoxycholate and benzalkonium chloride.

6. The method according to claim 2, in which the composition further comprises a detergent selected from the group consisting of sodium deoxycholate and benzalkonium chloride.

7. The method according to claim 6, in which the composition further comprises a detergent selected from the group consisting of sodium deoxycholate and benzalkonium chloride.

8. The method according to claim 4, in which the composition further comprises a detergent selected from the group consisting of sodium deoxycholate and benzalkonium chloride.

9. The method according to claim 1, in which the composition further comprises chlorhexidine and sodium deoxycholate in an amount such that the combination of silver sulfadiazine, chlorhexidine and sodium deoxycholate has an antiviral effect.

* * * * *

UNITED STATES PATENT AND TRADEMARK OFFICE
CERTIFICATE OF CORRECTION

PATENT NO. : 5,334,588
DATED : August 2, 1994
INVENTOR(S) : Charles L. Fox, Jr., deceased It is certified that error appears in the above-identified patent and that said Letters Patent is hereby corrected as shown below:

Col. 1, line 43, "vital" should read -- viral --; line 55, "vital" should read -- viral --. Col. 2, line 18 "humans for example," should read -- humans, for example, --. Col. 3, line 32, "palmirate" should read -- palmitate --; line 53, "AgED", each occurrence, should read -- AgSD --. Col. 8, lines 34 and 35, "immunofluorescense" should read -- immunofluorescence--; line 35, "vital" should read -- viral --. Cols. 9 and 10, Table 1, under "Material", "HTVL-III", each occurrence, should read -- HTLV-III --. Col. 11, line 6, "*AgSD +" should read -- "*AgSD → --; line 7, "+ Cell" should read -- → Cell--. Col. 12, line 13, "drug." should read -- drugs.--; line 13, "minute" should read -- minutes --; 4th line under Table 5B, "foring the" should read -- forming the --. Col. 13, line 8, "gonoccccus" should read -- gonococcus --; line 17, "incubatwd" should read -- incubated --; line 36, "Effect of" should read -- Effect on --; line 37, "w diluted" should read -- was diluted --; line 39, "titred" should read -- titered --. Col. 14, line 31, claim 7, "claim 6" should read -- claim 3 --.

Signed and Sealed this

Twelfth Day of September, 1995

Attest:

BRUCE LEHMAN

Attesting Officer     Commissioner of Patents and Trademarks